United States Patent [19]

Meilland

[11] Plant 5,042

[45] Apr. 26, 1983

[54] ROSE PLANT—MEIROBIDOR VARIETY

[75] Inventor: Marie L. Meilland, Antibes, France

[73] Assignee: The Conard-Pyle Company, West Grove, Pa.

[21] Appl. No.: 317,761

[22] Filed: Nov. 3, 1981

[30] Foreign Application Priority Data

Nov. 3, 1980 [NL] Netherlands ..... ROO 1041

[51] Int. Cl.[3] ..... A01H 5/00

[52] U.S. Cl. ..... Plt./15

[58] Field of Search ..... Plt./15

*Primary Examiner*—Robert E. Bagwill

*Attorney, Agent, or Firm*—Burns, Doane, Swecker & Mathis

[57] ABSTRACT

A new and distinct variety of Hybrid Tea rose plant is provided which is particularly suited for forcing in greenhouses to produce in a relatively rapid flower cycle long lasting highly attractive yellow flowers. The cut buds of the new variety open consistently and uniformly when placed in water. Also, the new variety exhibits above-average resistance to diseases which commonly afflict yellow-flowering roses.

18 Drawing Figures

SUMMARY OF THE INVENTION

The object of the present invention is to provide a new variety of rose plant of the Hybrid Tea Class which is distinguished from prior varieties by the following combination of characteristics:

(a) an erect growth habit, (b) the abundant formation of attractive long lasting and relatively non-fading yellow flowers in a rapid flower cycle, (c) the ability of the cut buds to open consistently and uniformly, and (d) above-average resistance to diseases which commonly afflict yellow-flowering roses.

In view of these characteristics the new variety meets the needs of the horticultural industry, and particularly is suited for forcing in greenhouses to produce cut flowers.

The new variety was created by artificial pollination whereby two parents which previously had been studied for the possession of the characteristics sought in the new variety were produced and combined.

The seed parent of the new variety resulted from the crossing of an unnamed variety (formed by the crossing of the Meialfi variety with an unnamed variety formed by the crossing of the Meger variety and the Meban variety) with the Golden Garnette variety (U.S. Plant Pat. No. 1,898). The pollen parent was an unnamed variety.

The parentage of the new variety may be expressed as follows:

[[Meialfi × (Meger × Meban)] × Golden Garnette] × Unnamed Variety

Selective study resulted in the identification of a single plant of the new variety. Extensive testing has confirmed the behavior and characteristics of the new variety.

The characteristics and properties of the new variety have been found to be transmissible by vegetative propagation, i.e. by grafting an eye.

The rose plant of the new variety has been named the Meirobidor variety.

BRIEF DESCRIPTION OF THE PHOTOGRAPH

The accompanying photograph shows as nearly true as it is reasonably possible to make the same in a color illustration of this character, typical specimens of plant parts from two year old plants cultivated in greenhouses during March at Cannet des Maures, Var, France illustrated in:

FIG. 1—a specimen of a young shoot;

FIG. 2—a specimen of a bud prior to the opening of the sepals;

FIG. 3—a specimen of a bud immediately after the opening of the sepals;

FIG. 4—a specimen of a bud as the petals begin to open;

FIG. 5—a specimen of a flower in the course of opening;

FIG. 6—a specimen of a flower when fully open;

FIG. 7—a specimen of a flower when fully open—plan view—obverse;

FIG. 8—a specimen of a flower when fully open—plan view—reverse;

FIG. 9—a specimen of a fully open flower immediately prior to petal drop—plan view—obverse;

FIG. 10—a specimen of a fully open flower immediately prior to petal drop—plan view—reverse;

FIG. 11—a specimen of a receptacle showing the arrangement of the stamens;

FIG. 12—a specimen of a receptacle showing the arrangement of the pistils (stamens removed);

FIG. 13—a specimen of a main branch;

FIG. 14—a specimen of a young flowering stem;

FIG. 15—a specimen of a leaf with three leaflets—upper surface;

FIG. 16—a specimen of a leaf with three leaflets—under surface;

FIG. 17—a specimen of a leaf with five leaflets—upper surface; and

FIG. 18—a specimen of a leaf with seven leaflets—upper surface.

DETAILED DESCRIPTION

Figures 1, 2, 3, 4, 5, 6, 7, 8, 9, 10, 11, 12, 13, 14, 15, 16, 17, 18:
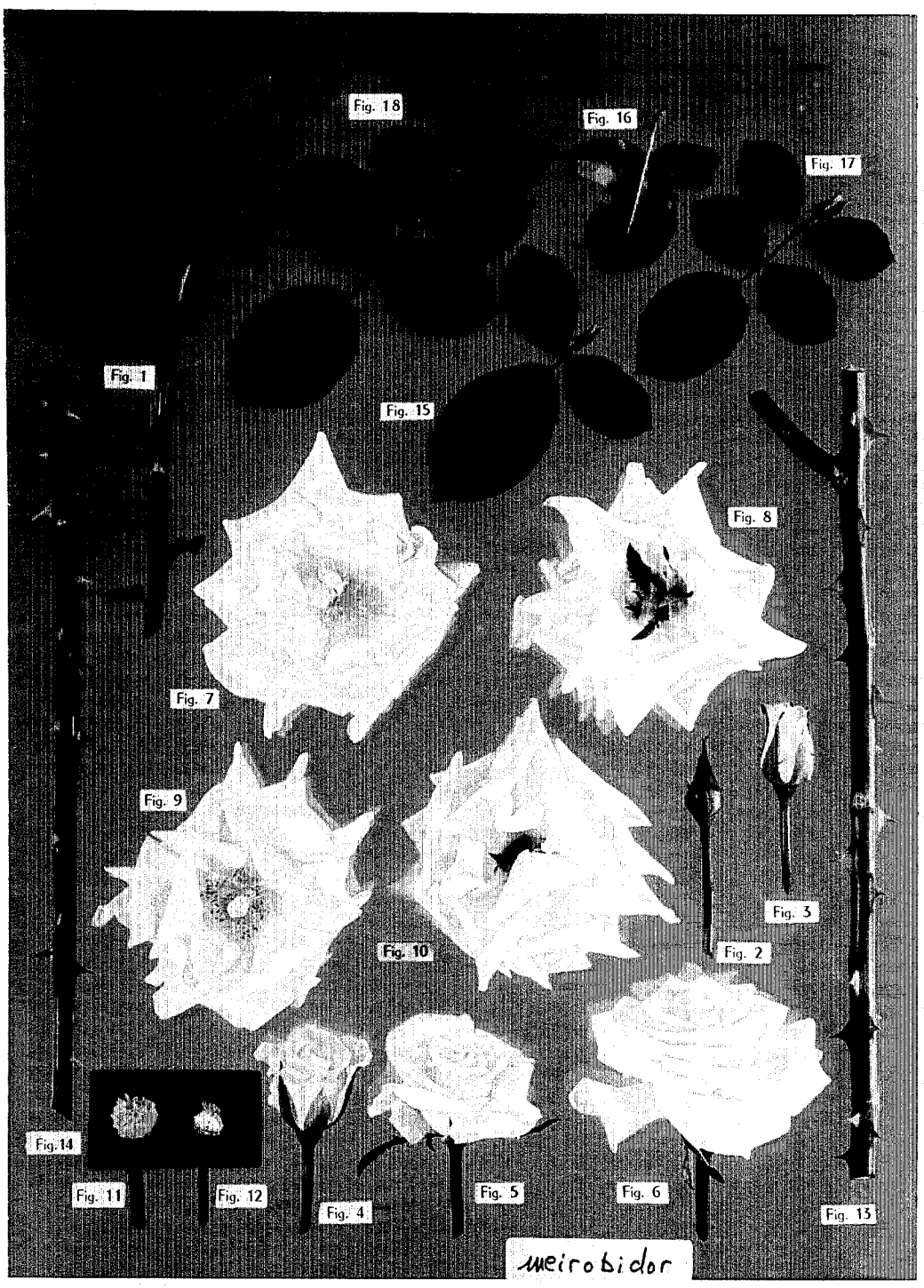

The plants described were grown under glass during March at Cannet des Maures, Var, France.

The chart utilized in the identification of the colors is that of The Royal Horticultural Society (R.H.S. Colour Chart). The terminology preceding the numbered references to this chart has been added to designate in common terms the corresponding colors.

Class: Hybrid Tea.

Plant:

*Height.*—Approximately 1.35 to 1.45 m. When cutting back to a height of approximately 0.85 m. in a greenhouse, cut flower bearing stems of approximately 0.5 to 0.6 m. may be obtained.

*Bearing.*—Erect.

Branches:

*Color.*—Young stems: bronze green 146A (Yellow-Green Group) with reddish shading. Mature wood: bronze green 146A (yellow-Green Group).

*Thorns.*—Shape: upper edge: straight, slender, slightly inflected towards the base. Lower edge: concave. Base: obovale. Color: reddish on young stems changing to Havana brown on mature wood.

Foliage:

*Leaflets.*—Number: commonly 3, 5, or 7. Size: medium. General appearance: semi-dull, fairly dense. Color: young foliage: dark green 147A (Yellow-Green Group). Color: mature foliage: dark green 147A (Yellow-Green Group).

Flowers:

*Number of flowers.*—Commonly one per stem; however, under forced conditions the first two auxiliary eyes under the initial flower sometimes also blossom.

*Buds.*—Length: medium. Shape: oblong.

*Flower.*—Form: double. Diameter: 13.5 cm. on average.

*Fragrance.*—Lacking.

*Lasting quality.*—Long.

*Petals.*—Number: 25 on average. Shape: rounded and slightly flattened.

*Color when first opening.*—Outside surface: lemon yellow 14B (Yellow-Orange Group) flushed with 16A (Yellow-Orange Group) on the edges. Inner surface: 14A (Yellow-Orange Group) and edged with a fine border of 16A (Yellow-Orange Group).

*Color when fully open.*—Outside surface: straw yellow 14C (Yellow-Orange Group) more or less flushed with 16C (Yellow-Orange Group) on the edges. Inner surface: lemon yellow 14B (Yellow-Orange Group) very slightly flushed with a fine border of 16B (Yellow-Orange Group).

*Color immediately prior to petal drop.*—Outer surface: 12C (Yellow Group) more or less flushed with 16D (Yellow-Orange Group) on the edges. Inner surface: 12B (Yellow Group) more or less flushed with 16C (Yellow-Orange Group) on the edges.

Occasionally a slight discoloration is observed on the edges of the petals particularly if the plant is grown under low temperature and low light conditions.

I claim:

1. A new and distinct variety of Hybrid Tea rose plant which is particularly suited for forcing in greenhouses, substantially as illustrated and described, characterized by an erect growth habit, the abundant formation of attractive long lasting and relatively non-fading yellow flowers in a rapid flower cycle, the ability of the cut buds to open consistently and uniformly, and above-average resistance to diseases which commonly afflict yellow-flowering roses.

* * * * * meirobidor